United States Patent
Van Liere et al.

(10) Patent No.: US 9,737,234 B2
(45) Date of Patent: Aug. 22, 2017

(54) LOW LATENCY SIGNALING OVER DIGITAL NETWORK

(75) Inventors: Filips Van Liere, Best (NL); Henricus Gerardus Roeven, Eindhoven (NL)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 1142 days.

(21) Appl. No.: 13/883,771

(22) PCT Filed: Nov. 7, 2011

(86) PCT No.: PCT/IB2011/054947
§ 371 (c)(1),
(2), (4) Date: May 14, 2013

(87) PCT Pub. No.: WO2012/063183
PCT Pub. Date: May 18, 2012

(65) Prior Publication Data
US 2013/0238286 A1    Sep. 12, 2013

Related U.S. Application Data

(60) Provisional application No. 61/410,995, filed on Nov. 8, 2010.

(51) Int. Cl.
*A61B 5/055* (2006.01)
*G01R 33/28* (2006.01)
*G06F 13/38* (2006.01)
*G01R 33/54* (2006.01)

(52) U.S. Cl.
CPC ............ *A61B 5/055* (2013.01); *G01R 33/288* (2013.01); *G01R 33/54* (2013.01); *G06F 13/38* (2013.01); *A61B 2560/0271* (2013.01); *G06F 2213/0038* (2013.01)

(58) Field of Classification Search
CPC ............ A61B 5/055; A61B 2560/0271; G01R 33/288; G01R 33/54; G06F 13/38; G06F 2213/0038
See application file for complete search history.

(56) References Cited

U.S. PATENT DOCUMENTS

| | | | | |
|---|---|---|---|---|
| 5,726,571 | A * | 3/1998 | Guclu | G01R 33/56518 324/307 |
| 6,198,283 | B1 * | 3/2001 | Foo | G01R 33/561 324/307 |
| 6,272,469 | B1 * | 8/2001 | Koritzinsky | A61B 5/0002 128/920 |
| 6,298,112 | B1 * | 10/2001 | Acharya | A61B 6/032 378/15 |
| 6,325,540 | B1 * | 12/2001 | Lounsberry | A61B 5/0002 378/114 |

(Continued)

FOREIGN PATENT DOCUMENTS

| EP | 2226002 A1 | 9/2010 |
|---|---|---|
| WO | 2008155703 A1 | 12/2008 |

*Primary Examiner* — Dixomara Vargas

(57) ABSTRACT

A diagnostic imaging system includes a first controller that detects any unsafe or dangerous conditions in a diagnostic scanner and generates safety/emergency data indicative of the unsafe or dangerous conditions. A communication unit generates a safety/emergency signal from the safety/emergency data using a digital protocol and communicates the safety/emergency over a local digital network.

20 Claims, 3 Drawing Sheets

(56) References Cited

U.S. PATENT DOCUMENTS

| | | | |
|---|---|---|---|
| 6,331,776 B1* | 12/2001 | Debbins | G01R 33/54 324/307 |
| 6,351,122 B1* | 2/2002 | Polzin | G01R 33/561 324/307 |
| 6,353,445 B1* | 3/2002 | Babula | A61B 5/0002 705/2 |
| 6,359,961 B1* | 3/2002 | Aufrichtig | A61B 6/022 348/E13.005 |
| 6,366,094 B1* | 4/2002 | Vassallo | G01R 33/54 324/312 |
| 6,377,162 B1* | 4/2002 | Delestienne | G06F 19/3412 340/286.07 |
| 6,381,557 B1* | 4/2002 | Babula | G06F 19/3412 434/322 |
| 6,412,980 B1* | 7/2002 | Lounsberry | G06F 19/3412 378/114 |
| 6,418,334 B1* | 7/2002 | Unger | G06F 19/3412 128/922 |
| 6,434,572 B2* | 8/2002 | Derzay | |
| 6,434,617 B1 | 8/2002 | Clough et al. | |
| 6,492,812 B1* | 12/2002 | Debbins | G01R 33/54 324/307 |
| 6,494,831 B1* | 12/2002 | Koritzinsky | G06F 19/3412 128/903 |
| 6,501,849 B1* | 12/2002 | Gupta | G06F 19/321 382/141 |
| 6,509,914 B1* | 1/2003 | Babula | G06F 19/324 715/762 |
| 6,546,230 B1* | 4/2003 | Allison | G09B 23/28 434/262 |
| 6,574,518 B1* | 6/2003 | Lounsberry | A61B 5/055 235/375 |
| 6,578,002 B1* | 6/2003 | Derzay | G06F 19/3412 705/2 |
| 6,598,011 B1* | 7/2003 | Howards Koritzinsky | G06F 19/321 382/141 |
| 6,603,494 B1* | 8/2003 | Banks | A61B 5/055 600/410 |
| 6,609,217 B1* | 8/2003 | Bonissone | G06F 11/2257 714/26 |
| 6,691,134 B1* | 2/2004 | Babula | A61B 6/00 |
| 6,731,798 B1* | 5/2004 | Stearns | A61B 6/581 382/172 |
| 6,832,199 B1* | 12/2004 | Kucek | A61B 5/0002 600/300 |
| 6,901,371 B1* | 5/2005 | Koritzinsky | A61B 5/0002 128/920 |
| 6,912,481 B2* | 6/2005 | Breunissen | A61B 6/032 702/182 |
| 6,988,074 B2* | 1/2006 | Koritzinsky | A61B 5/0002 128/920 |
| 7,050,984 B1* | 5/2006 | Kerpelman | G06F 19/3412 600/300 |
| 7,055,062 B2* | 5/2006 | Shah | G05B 23/0224 714/15 |
| 7,080,095 B2* | 7/2006 | Accardi | G06F 19/321 |
| 7,127,499 B1* | 10/2006 | Accardi | G06F 19/327 709/201 |
| 7,219,222 B1* | 5/2007 | Durbin | G06F 21/305 705/51 |
| 7,225,406 B2* | 5/2007 | Babula | G06F 19/324 715/736 |
| 7,263,710 B1* | 8/2007 | Hummel, Jr. | G06F 19/324 434/262 |
| 7,269,243 B2* | 9/2007 | Chell | A61B 6/032 378/18 |
| 7,451,002 B2* | 11/2008 | Choubey | G05B 23/0283 128/898 |
| 7,620,142 B1* | 11/2009 | Toth | A61B 6/032 378/108 |
| 7,673,081 B2 | 3/2010 | Grottel et al. | |
| 7,703,020 B2* | 4/2010 | Bhattaru | G06F 19/3418 600/300 |
| 7,860,551 B2* | 12/2010 | Sugimoto | A61B 5/055 324/309 |
| 7,890,887 B1 | 2/2011 | Linardos et al. | |
| 8,204,832 B2* | 6/2012 | Minagawa | A61B 5/055 705/2 |
| 8,416,076 B2* | 4/2013 | Mamourian | G01B 31/318547 324/200 |
| 8,554,902 B2* | 10/2013 | Ebert | G06F 19/3412 709/217 |
| 9,186,127 B2* | 11/2015 | Kurt | A61B 8/467 |
| 2003/0214953 A1 | 11/2003 | El-Demerdash et al. | |
| 2005/0129028 A1 | 6/2005 | Peeters | |
| 2008/0114923 A1 | 5/2008 | In | |
| 2010/0199004 A1 | 8/2010 | Lin | |
| 2011/0170667 A1 | 7/2011 | Ruggiero et al. | |
| 2011/0261814 A1 | 10/2011 | Matthews | |

* cited by examiner

LOW LATENCY SIGNALING OVER DIGITAL NETWORK

CROSS REFERENCE TO RELATED APPLICATIONS

This application is a national filing of PCT application Serial No. PCT/IB2011/054947, filed Nov. 7, 2011, published as WO 2012/063183 A2 on May 18, 2012, which claims the benefit of U.S. provisional application Ser. No. 61/410,995 filed Nov. 8, 2010, which is incorporated herein by reference.

FIELD OF THE INVENTION

The present application relates to the diagnostic imaging arts. It finds particular application in the communication of safety and emergency information over a digital network in a magnetic resonance imaging (MRI) system, and will be described with particular reference thereto. It is to be understood, however, that it also finds application in other imaging devices, and is not necessarily limited to the aforementioned application.

BACKGROUND OF THE INVENTION

Currently, magnetic resonance imaging systems use a backplane bus in order to communicate safety and emergency information. The backplane bus includes an array of dedicated signal wires to communicate safety and emergency information to various safety and interlock mechanisms of the MRI system. Safety and emergency information is critical, for example, in controlling the state of the RF transmit/receive switch but is also applicable to various other system states and controlling corresponding devices in the MRI system including the gradient amplifiers, cooling system, and the like.

For example, before an RF transmitter is activated to try and transmit an RF pulse during a magnetic resonance (MR) imaging sequence, one must be sure that the RF receiver is in the OFF or disconnected state. Transmitting an RF pulse, which is a relatively high power pulse, when the RF amplifier is configured to receive relatively weak resonance signals, could damage the RF receiver. Due to the speed at which pulses are applied and echoes are received in the MR imaging sequence, this information must be communicated with very low latency and independent of normal software device control functions to ensure the RF amplifier and RF receiver are not in the ON or connected state at the same time.

Dedicated signal wires ensure the safe operation of the MRI system by providing an independent low latency communication of safety and emergency information to the various safety and interlock mechanisms. Although the dedicated signal wires provide a solution to satisfy these safety requirements, the increasing complexity of MRI systems increases the cost and physical complexity of the implementation of a backplane bus and/or signal wires to communicate safety and emergency information.

The present application provides a new and improved system and method for communicating safety and emergency information which overcomes the above-referenced problems and others.

BRIEF SUMMARY OF THE INVENTION

In accordance with one aspect, a diagnostic imaging system is provided. A first controller detects any unsafe or dangerous conditions in a diagnostic scanner and generates safety/emergency data indicative of the unsafe or dangerous conditions. A communication unit generates a safety/emergency signal from the safety/emergency data using a digital protocol and communicates the safety/emergency over a local digital network.

A method of communicating safety/emergency data in a diagnostic imaging system is provided. Unsafe or dangerous conditions are detected in the diagnostic imaging system. Safety/emergency data indicative of the unsafe or dangerous conditions is generated. A safety/emergency signal is generated from the safety/emergency data using a digital protocol. The safety/emergency signal is transmitted over a local digital network.

One advantage resides in the low latency transmission of safety and emergency information.

Another advantage resides in the independent communication of safety and emergency information.

Another advantage resides in the decreased cost and complexity of communicating safety and emergency information.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE INVENTION

Figure 1:
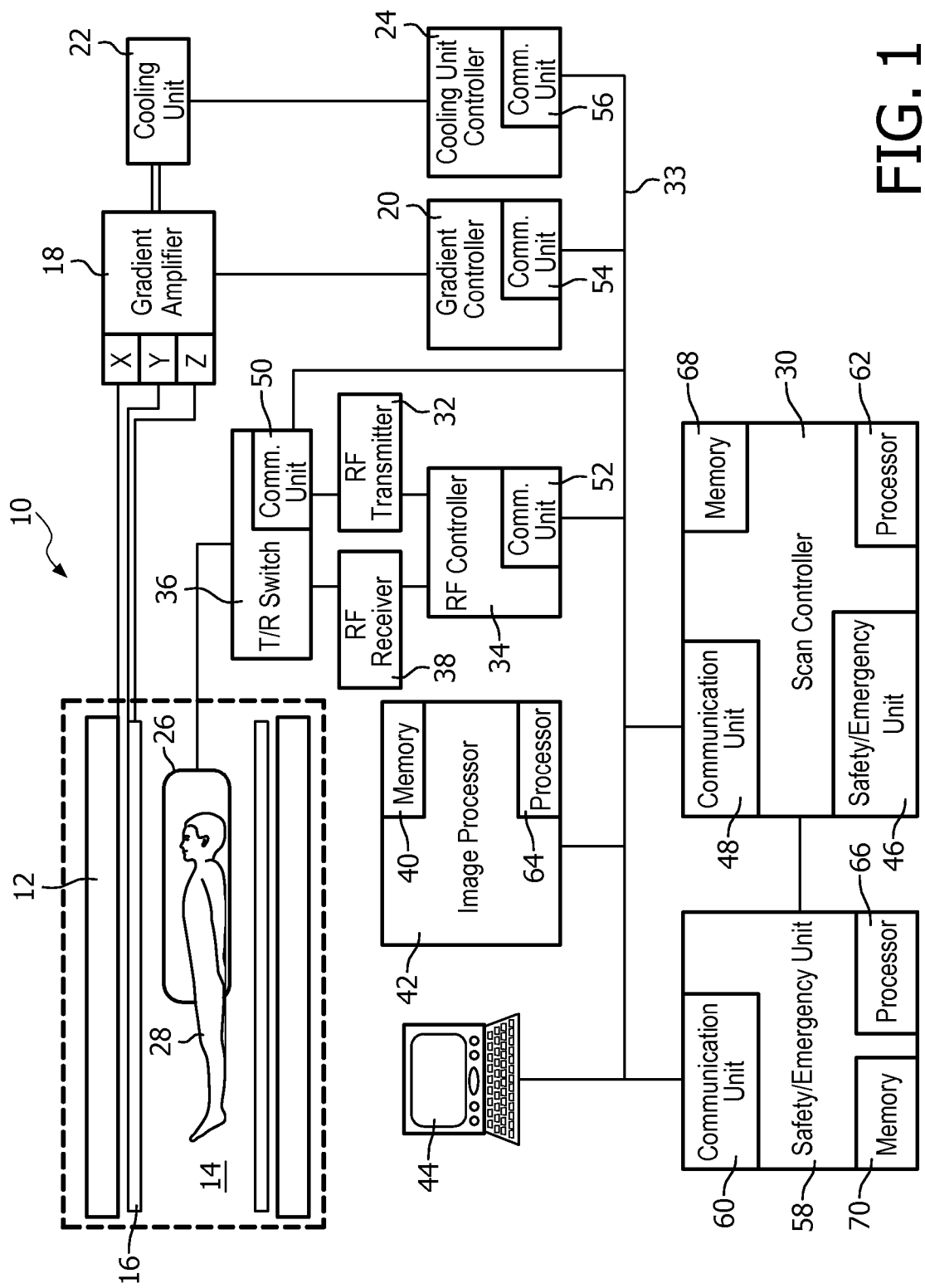
FIG. 1 is a diagrammatic illustration of an imaging system in accordance with the present application.

With reference to FIG. 1, a magnetic resonance imaging (MRI) system 10 includes a main magnet 12 which generates a spatial and temporally uniform $B_0$ field through an examination region 14. The main magnet 12 can be an annular or bore-type magnet, a C-shaped open magnet, other designs of open magnets, or the like.

Gradient magnetic field coils 16 disposed adjacent the main magnet 12 serve to generate magnetic field gradients along selected axes relative to the $B_0$ magnetic field for spatially encoding magnetic resonance signals, for producing magnetization-spoiling field gradients, or the like. The gradient magnetic field coil 16 may include coil segments configured to produce magnetic field gradients in three orthogonal directions, typically longitudinal or z, transverse or x, and vertical or y directions. A gradient amplifier unit 18, controlled by a gradient controller 20, includes a plurality of amplifiers to generate the magnetic field gradients in the three orthogonal directions. Each gradient amplifier excites a corresponding gradient magnetic field coil 16 to produce the magnetic field gradients. A cooling unit 22, controlled by a cooling unit controller 24, cools the gradient amplifiers and gradient magnetic field coils 16 through a series of cooling ducts, a chiller, a water cooled refrigeration condenser, liquid cooling circuits, and the like.

The system 10 includes a radio-frequency (RF) coil assembly 26 disposed in or adjacent to the examination region 14. Although illustrated surrounding the patient, head coils, flexible and rigid surface coils, and other coils that are mounted on upper and side surfaces of the patient, that wrap around the torso or limbs, and the like are also contemplated. Although only a whole body RF coil assembly 26 is illustrated for simplicity of illustration, the whole body coil for transmit and a plurality of RF receive coil assemblies are contemplated. The coil assembly 26 includes multiple coil elements which, during operation, alone or collectively generate radio frequency fields for exciting magnetic resonance in one or more nuclear species, such as $^1H$, $^{13}C$, $^{31}P$, $^{23}Na$, $^{19}F$, or the like. The radio-frequency coil assemblies 26, alone or collectively, or the one or more receive coils (not shown) serve to detect magnetic resonance signals emanating from the imaging region.

To acquire magnetic resonance data of a subject 28, the subject is positioned inside the examination region 14 by a patient support, with a region of interest preferably at or near the isocenter of the main magnetic field. A scan controller 30 controls the gradient controller 20 via a digital network 33 to generate selected magnetic field gradient pulses from the gradient amplifier 18 and to apply the selected magnetic field gradient pulses across the imaging region through the gradient magnetic field coils 16, as may be appropriate to a selected magnetic resonance imaging or spectroscopy sequence. The scan controller 32 also controls the cooling unit controller 24 via the digital network 33 to cool the gradient amplifiers and gradient magnetic field coils 16. The scan controller 32 also controls one or more RF transmitters 32, through a RF controller 34, via the digital network 33 to generate unique radio-frequency signals to generate magnetic resonance excitation and manipulation $B_1$ pulses.

The scan controller 30 also controls an RF receiver 38 via the digital network 33, through the RF controller 34, to receive the induced magnetic resonance signals from the subject. In the embodiment in which the same coil transmits and receives, a transmit/receive switch 36 serves to switch the conductors between signal transmissions from the RF transmitter 32 and signal reception to the RF receiver 38. In the embodiment with separate receive coils, the scan controller 30 controls the transmit/receive switch 36 via the digital network 33 to switch the receive coils and/or the receiver 38 to switch between a receive mode and a detuned mode. The received data from the RF receiver 38 is communicated over the digital network 33 and temporarily stored in an image memory 40 and processed by a magnetic resonance image, spectroscopy, or other image processor 42. The magnetic resonance data processor can perform various functions as are known in the art, including image reconstruction (MRI), magnetic resonance spectroscopy (MRS), catheter or interventional instrument localization, and the like. Reconstructed magnetic resonance images, spectroscopy readouts, interventional instrument location information, and other processed MR data are stored in memory, such as a medical facility's patient archive. A graphic user interface or display device 44 includes a user input device which a clinician can use for controlling the scan controller 30 via the digital network 33 to select scanning sequences and protocols, display MR data or reconstructed MR images, and the like.

The scan controller 30 also includes a safety/emergency unit 46 which generates safety/emergency data in response to detecting unsafe or dangerous conditions in the MRI system 10 or during the MR imaging sequence. The safety/emergency unit 46 observes and evaluates the operation of the MRI system 10 to determine if any unsafe or dangerous conditions are present. In one embodiment, the scan controller 30 observes the operation of the MRI system 10 through operating or safety/emergency data received via the digital network 33 from the RF controller 34, the gradient controller 20, the cooling unit controller 24, and other system components. The scan controller 30 includes a communication unit 48 to receive the safety/emergency data via the digital network 33. The unsafe or dangerous conditions may include the RF transmitter 32 and RF receiver 38 being in the ON or connected state at the same time, the cooling unit 22 malfunctioning, the gradient magnetic field coils 16 overheating, and the like. In response to detecting an unsafe or dangerous condition, the safety/emergency unit 46 of the scan controller 30 generates safety/emergency data indicative of the unsafe or dangerous condition and communicates the safety/emergency data to the communication unit 48 in the scan controller 30. The communication unit 48 generates safety/emergency signals from the safety/emergency data and communicates the safety/emergency signals to communication units 52, 54, 56 in the RF controller 34, the gradient controller 20, the cooling unit controller 24, and other system components over the digital network 33 such as one or more optical fiber networks, an Ethernet, IEEE802.11, and other Internet Protocol (IP) centric access networks (RapidIO, General Packet Radio Service (GPRS), CDMA 2000, Wireless LAN, mobile WIMAX), and the like.

The communication unit 48 in the scan controller 30 and the communication units utilize an industry standard digital protocol, such as RapidIO serial protocol, to transmit the safety/emergency signal over local digital networks 33. Preferably, the standard digital protocol is an extension of a packet based digital network protocol that has codes available for out-of-band transport of symbols. Typically, such digital network protocols have three levels of data transfers including a character level, a symbol level, and a packet level. The communication units 48, 50, 52, 54, 65 generate the safety/emergency signals using the standard digital protocol to insert newly defined or custom symbols in unused portions of the symbol level that are indicative of the safety/emergency data. The safety/emergency signals include the newly defined symbols such that in response to receiving the safety/emergency signal, the scan controller 30, the RF controller 34, the T/R switch 36, the gradient controller 20, the cooling unit controller 24, and other components control the corresponding devices of the MRI system 10 to properly respond to the unsafe or dangerous conditions. For example, if the safety/emergency signal is indicative of the RF transmitter and RF receiver being in the ON or connected state at the same time; the RF controller or the T/R switch on their own initiative or under control of the scan controller 30 disconnects one of either the RF transmitter or RF receiver. In response to receiving a safety/emergency signal indicative of a malfunctioning cooling unit or overheating gradient amplifiers, the gradient controller disables the gradient amplifiers.

In another embodiment, the scan controller 30 controls a safety/emergency unit 58 to generate safety/emergency data in response to receiving component state signals from the communication units 50-56 indicative of unsafe or dangerous conditions detected in the MRI system 10 or during the MR imaging sequence. The safety/emergency unit 58 observes and evaluates the operation of the MRI system 10 to determine if any unsafe or dangerous conditions are detected. In response to determining an unsafe or dangerous condition, the safety/emergency unit 58 generates safety/emergency data indicative of the unsafe or dangerous condition. The safety/emergency unit 58 communicates the safety/emergency data to a communication unit 60 in the safety/emergency unit 58. The communication unit 60 generates a safety/emergency signal from the received safety/emergency data and communicates the safety/emergency signal over local digital networks 33.

The gradient controller 20, the cooling unit controller 24, the scan controller 30, the RF controller 34, the image processor 42, and the emergency safety unit 58 also include a processor 62, 64, 66, for example a microprocessor or other software controlled device configured to execute MRI control software for performing the operations described in further detail below. Typically, the MRI control software is carried using tangible memory 40, 68, 70 or a computer readable medium for execution by the processor. Types of computer readable media include memory such as a hard disk drive, CD-ROM, DVD-ROM and the like. Other implementations of the processor are also contemplated. Display controllers, Application Specific Integrated Circuits (ASICs), FPGAs, and microcontrollers are illustrative examples of other types of component which may be implemented to provide functions of the processor. Embodiments may be implemented using software for execution by a processor, hardware, or some combination thereof.

As previously described, the system utilizes an industry standard digital protocol, preferably RapidIO, to transmit signals containing custom control symbols over the local digital network 33. Preferably, the standard digital protocol utilizes serial optical connection mediums and includes a full duplex serial physical layer interface between devices using unidirectional differential signals in each direction. The standard defines protocol for packet delivery between serial devices including packet and control symbol transmission, flow control, error management acknowledgements, and other device to device functions. The serial devices include logic in the physical transport layer implementation both to generate and interpret the standard digital protocol. The standard digital protocol is designed to satisfy the safety requirements of low-latency and independent operation while co-existing with other protocols on the local digital network 33 and thus enables the elimination of dedicated cabling solutions. As mentioned above, the protocol is an extension to packet based digital network protocols that have codes available for out-of-band transport of symbols. The standard digital protocol typically includes three levels of data transfer: character, symbol and packet. One such protocol is the industry standard RapidIO protocol. The character level typically contains 8-10 bit coding and includes "1"s and "0"s which are transmitted over the local digital network 33. The symbol level typically includes 32 or 40 bits and is used to carry protocol maintenance information, link utility function, packet acknowledgements, and packet delineation. The packet level carries packets of conventional digital information.

Figure 2:
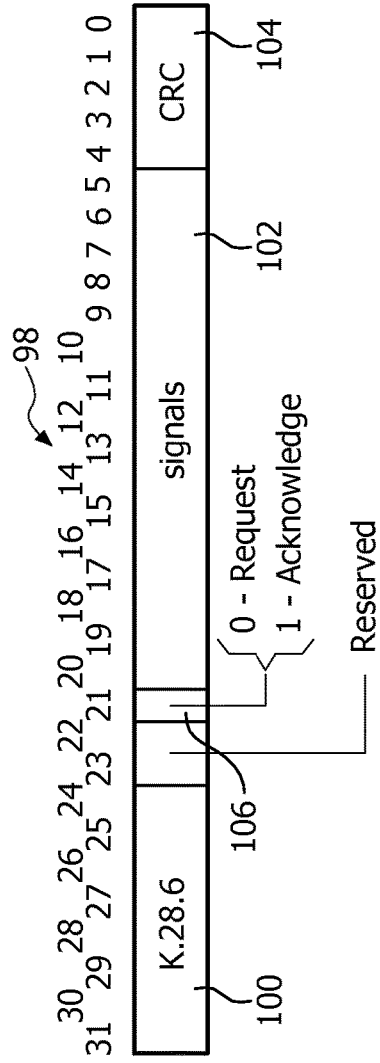
FIG. 2 is a diagrammatic illustration of a safety/emergency signal in accordance with the present application.

With reference to FIG. 2, a safety/emergency signal implemented via the custom standard digital protocol symbol is illustrated. The standard digital protocol has a number of predefined symbol codes. The safety/emergency signal 98 utilizes unused symbol codes 100 that are different from the standard symbol codes of the standard digital protocol to transfer a limited number (for example 16) of binary signal values 102. The transfer latency of such symbols is limited by the size of the symbol (32 or 40 bits for RapidIO) and the bit-rate of the network. For minimal latency, the symbol pre-empts any packet transfer that is in progress. This ensures that the latency is independent of other network usage. The unused symbol code 100 is defined for the indication of an unsafe or dangerous condition detected in the MRI system or during the MR imaging sequence. Logic is inserted in the physical transport layer implementations of the various communication units 48-56 and devices in the MRI system to generate and interpret the newly defined or custom symbols codes 100.

The signals values 102 in the safety/emergency signal are a series of single bits of digital information that are transmitted with extremely low latency (in the order of microseconds). The signal values 102 include the safety/emergency data indicative of the unsafe or dangerous condition. The signal values 102 are defined such that each unsafe or dangerous condition is given an individual value that can be interpreted by the communication units. Logic is inserted in the physical transport layer implementations of the various communication units 48-56 and devices in the MRI system to generate and interpret the newly defined or custom signal value 102. For example, when a communication unit receives the newly defined symbol code indicative of unsafe or dangerous condition in the MRI system or during the MR imaging sequence, the communication unit interprets the signals values to determine which unsafe or dangerous condition exists which is then communicated to the corresponding controller. A list of typically allocated signals is given below.

| Signal (102) | Description |
| --- | --- |
| RESET | Reset devices. |
| START | Start enabled stretch engines. |
| ERROR | Anonymous error occurred. |
| ATTENTION | A device on the network requires attention. |
| DETUNE_1H | Detune selected 1H coil elements. |
| INTER_REQ_1H | Request 1H receiver interlock status. |
| INTER_ACK_1H | Acknowledge 1H receiver interlock status. |
| DETUNE_MN | Detune selected multi-nuclear coil elements. |
| INTER_REQ_MN | Request multi-nuclear receiver interlock status. |
| INTER_ACK_MN | Acknowledge multi-nuclear receiver interlock status. |

The local digital network typically can transmit 16 signals in one direction from the communication unit 48, 60 and 16 signals in another direction from the communication units 50-56 over each individual link. The defined 16 signal values 102 are transferred simultaneously by a single symbol code 100. A common symbol code can be used to identify an emergency communication or a plurality of symbol codes can be used to identify different type of emergency communications. Across each link we can send 16 of these signal values simultaneously. Signal transmission is implemented using the newly defined symbol codes 100. Because the symbol can be a 32 or 40 bit value that can be transmitted asynchronously, the signal transmission can be propogated over the network with very low latency. The emergency signal transmission can be inserted between or in the middle of other communication to achieve low latency reliable transmissions of safety/emergency information. When a signal value changes, a signal request symbol 106 is sent over the link, transferring the state of all 16 signal values 102. When a signal request symbol is received, a signal acknowledge symbol 106 is returned. As long as signals are not acknowledged, signal requests are (re-) transmitted. An error correction (CRC) component 104 along with the acknowledgement components assures reliable error-free transmissions.

Transmission of the safety/emergency signal also preempts normal packet delivery and can be injected at any particular time as long as synched to the delivery frames on the physical link. At any 40 bit frame, a 40 bit coded symbol which preempts the transmission of the packet can be sent. In such a situation, the only latency present would be the 40 bit frame on the actual link. If transmission of the safety/emergency signal preempts the transmission of a packet during the 40 bit frame, the packet continues transmission after the code symbol has been successfully communicated. The protocol may also be implemented in firmware (for example in VHDL on an FPGA or in an ASIC) that can be operated and validated independently of normal (typically software based) device control functions. Such an implementation eliminates the dependence on (correctly) operating software, ensuring that the required signalling operates in the absence of software or in the presence of failing software.

Figure 3:
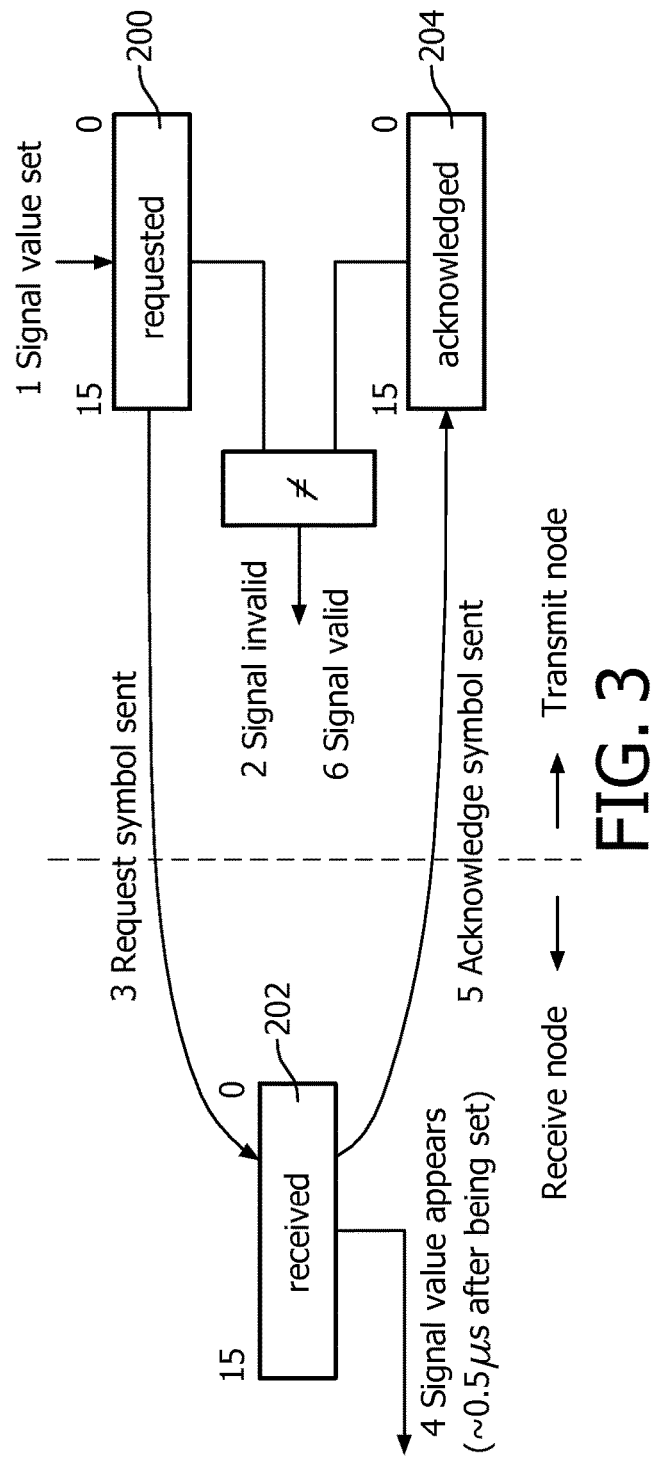
FIG. 3 is a diagrammatic illustration of the logic for error-free transmission of a safety/emergency signal in accordance with the present application.

FIG. 3 illustrates logic for the error-free reliable transmission of the safety/emergency signal 98. A requested register 200 in each communication unit holds the symbol code and signal values of a safety/emergency signal. A received register 202 in the receiving communication unit holds the safety/emergency signal received without error. An acknowledged register 204 in the sending communication unit holds the symbol code and signal values of the safety/emergency signal that have been acknowledged without error by the receiving register 202. A timer is used to avoid saturating the link with signal requests. A new signal request is not transmitted as long as the timer has not expired. If the requested safety/emergency signal is not equal to the acknowledged safety/emergency signal than an error has occurred in the transmission of the safety/emergency signal. If the timer has expired then the communication unit re-transmits the safety/emergency signal and restarts the timer. If a safety/emergency signal is received without error then the safety/emergency signal is stored in the acknowledged register 204 and the timer is stopped. If a safety/emergency signal stored in the acknowledge register 204 is received with CRC error, the error is ignored.

If the timer expires and a requested safety/emergency signal has still not been acknowledged then a re-transmit request will be sent. If the re-transmitted safety/emergency signal is received at the received register 202 without error then the signal is stored and the acknowledged safety/emergency signal is sent to the acknowledged register 204. If the acknowledgment signal received in the acknowledgement register 204 is received with a CRC error, the error is ignored. If the requested safety/emergency signals change rapidly then it is possible these changes are not reflected at the receiving register 202 because there is a limit at which the safety/emergency signals can be transmitted. This occurs when the safety/emergency signals change faster than that they can be acknowledged.

Figure 4:
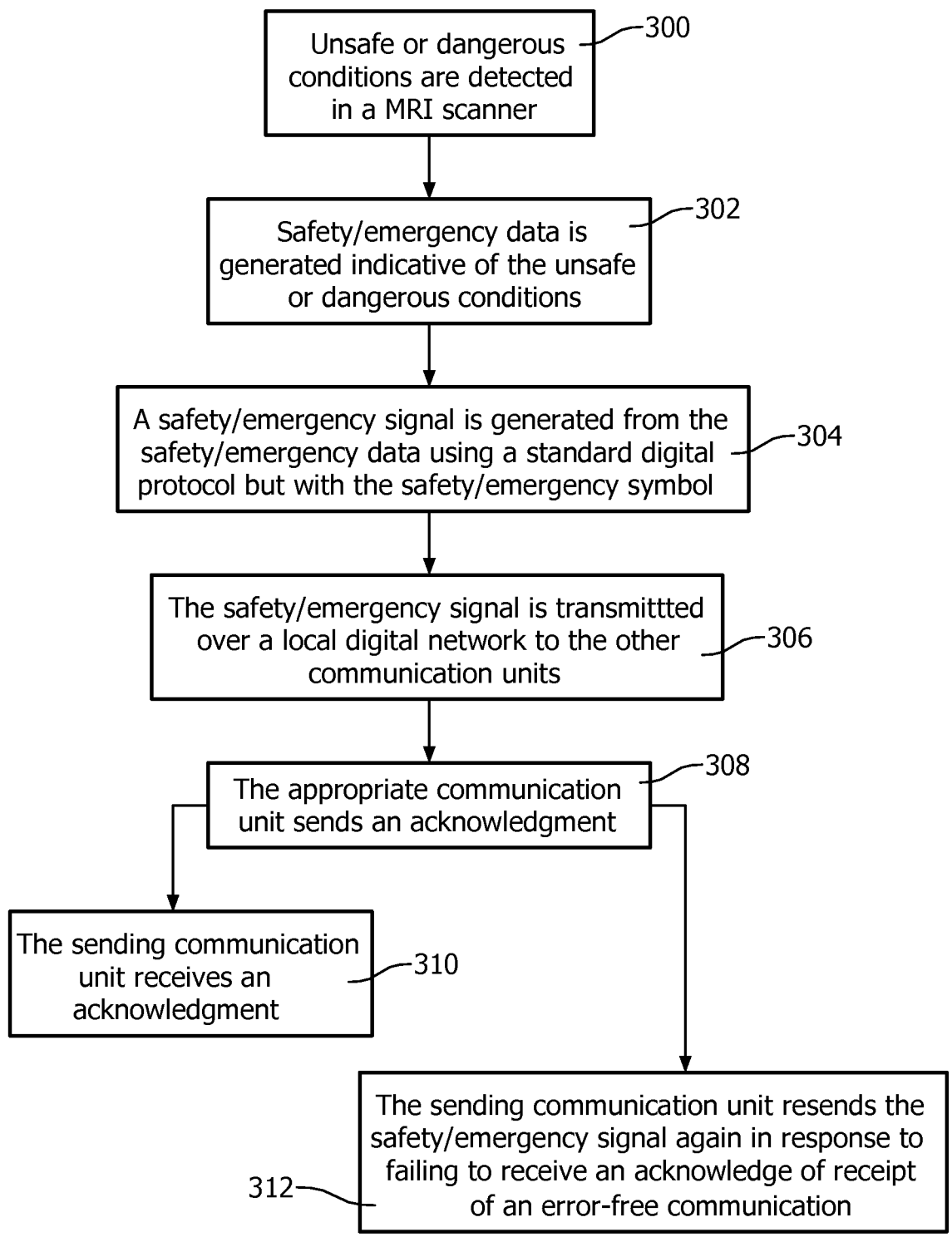
FIG. 4 is a diagrammatic illustration of a method for communicating a safety/emergency signal in accordance with the present application.

FIG. 4 illustrates a method of communicating a safety/emergency signal. In a step 300, unsafe or dangerous conditions are detected in a MRI scanner. Safety/emergency data is generated indicative of the unsafe or dangerous conditions in a step 302. In a step 304, a safety/emergency signal is generated from the safety/emergency data using a standard digital protocol but with the safety/emergency symbol 100. The safety/emergency signal is transmitted over a local digital network 33 to the other communication units. The appropriate communication unit sends an acknowledgment at a step 308. At a step 310, the sending communication unit receives an acknowledgment or at a step 312, the sending communication unit resends the safety/emergency signal 98 again in response to failing to receive an acknowledge of receipt of an error-free communication.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A diagnostic imaging system comprising:
   a first controller that detects any unsafe or dangerous conditions in a diagnostic scanner and generates safety/emergency data indicative of the unsafe or dangerous conditions;
   a communication unit that generates a safety/emergency signal from the safety/emergency data using a digital protocol and communicates the safety/emergency over a local digital network;
   wherein the communication unit that generates the safety/emergency signal preempts normal packet delivery over the local digital network and inserts the safety/emergency signal onto the local digital network.

2. The system according to claim 1, wherein the digital protocol defines protocol for packet delivery between serial devices including three levels of data transfer: a character level, a symbol level, and a packet level.

3. The system according to claim 1, wherein the communication unit generates the safety/emergency signal using the digital protocol to insert a custom symbol indicative of the safety/emergency data using otherwise unused symbol codes.

4. The system according to claim 1, wherein the digital protocol is configured to preempt by interrupting mid packets.

5. The system according to claim 1, wherein the communication unit includes firmware and operates independently of the diagnostic imaging system functions to generate the safety/emergency signal.

6. The system according claim 1, wherein the diagnostic imaging system includes a magnetic resonance system having an RF transmitter and an RF receiver and wherein the unsafe or dangerous conditions includes: the RF transmitter and RF receiver being in an ON or connected state at the same time.

7. The system according to claim 1, wherein the local digital network includes a fiber optic network over which the safety/emergency signals are optically transmitted.

8. The system according to claim 1, wherein the communication of the safety/emergency signal includes an CRC error detection component.

9. A method of communicating safety/emergency data in a diagnostic imaging system, the method comprising:
   with at least one controller, detecting unsafe or dangerous conditions in the diagnostic imaging system;
   with the at least one controller, generating safety/emergency data indicative of the unsafe or dangerous conditions;
   with a communication unit, generating a safe/emergency signal from the safety/emergency data using a digital protocol; and
   with the communication unit, transmitting the safety/emergency signal over a local digital network, wherein the transmission of the safety/emerge signal preempts normal packet delivery over the local digital network.

10. The method according to claim 9, wherein the digital protocol defines protocol for packet delivery between serial devices including three levels of data transfer: a character level, a symbol level, and a packet level.

11. The method according to claim 9, wherein the safety/emergency signal includes a custom symbol component, an acknowledgement/request component, safety/emergency data, and a error check component.

12. The method according to claim 9, wherein the digital protocol is a standard networking protocol with custom symbols different from symbols of the standard networking protocol to identify the safety/emergency signal.

13. The method according to claim 9, wherein the diagnostic imaging system includes a magnetic resonance system having an RF transmitter and an RF receiver and wherein the unsafe or dangerous conditions includes: the RF transmitter and RF receiver being in an ON or connected state at the same time.

14. A non-transitory computer readable medium carrying software which control one or more processors to perform the method according to claim 9.

15. An magnetic resonance imaging (MRI) system comprising:
 a main magnet configured to define an imaging bore;
 a support configured to support a subject into and along the bore;
 a gradient coil configured to create magnetic field gradients in the imaging bore;
 an RF transmitter coil configured to transmit RF pulses into the imaging bore;
 an RF receiver coil configured to receive the induced RF pulses; and
 one or more processors programmed to perform the method according to claim 9.

16. A diagnostic imaging system comprising:
 at least one gradient coil configured to create magnetic field gradients in an imaging bore defined by a main magnet;
 a cooling unit configured to cool the at least one gradient field coil;
 an RF transmitter coil configured to transmit RF pulses into the imaging bore;
 an RF receiver coil configured to receive the induced RF pulses;
 at least one processor programmed to detect at least one of: overheating of the at least one magnetic field coil; a malfunction of the cooling unit; and the RF transmitter and the RF receiver being in an ON or connected state simultaneously;
 wherein the at least one processor includes at least one communication unit configured to generate a respective signal from the corresponding detection of the overheating of the at least one magnetic field coil, the malfunction of the cooling unit, and the RF transmitter and the RF receiver being in an ON or connected state simultaneously, the at least one communication unit being configured to communicate the respective signal over a local digital network to preempt normal packet delivery over the local digital network and inserting the respective signal onto the local digital network.

17. The system according to claim 16, wherein the digital protocol defines protocol for packet delivery between serial devices including three levels of data transfer: a character level, a symbol level, and a packet level.

18. The system according to claim 16, wherein the at least one communication unit generates the respective signal using the digital protocol to insert a custom symbol indicative of the respective signal using otherwise unused symbol codes.

19. The system according to claim 16, wherein the digital protocol is configured to preempt by interrupting mid packets.

20. The system according to claim 16, wherein each communication unit includes firmware and operates independently of the diagnostic imaging system functions to generate each respective signal.

* * * * *